(12) United States Patent
Howes et al.

(10) Patent No.: US 11,957,650 B2
(45) Date of Patent: Apr. 16, 2024

(54) FORMULATION AND METHOD FOR THE PREVENTION AND/OR TREATMENT OF HANGOVER SYMPTOMS

(71) Applicant: PHOENIX PHARMACEUTICALS AUSTRALIA PTY LTD, Hope Island (AU)

(72) Inventors: Laurence Guy Howes, Hope Island (AU); Jan Beatrice Quinton, Hope Island (AU)

(73) Assignee: PHOENIX PHARMACEUTICALS AUSTRALIA PTY LTD, Hope Island (AU)

( * ) Notice: Subject to any disclaimer, the term of this patent is extended or adjusted under 35 U.S.C. 154(b) by 0 days.

(21) Appl. No.: 17/227,020

(22) Filed: Apr. 9, 2021

(65) Prior Publication Data

US 2021/0220313 A1    Jul. 22, 2021

Related U.S. Application Data

(63) Continuation of application No. 16/087,563, filed as application No. PCT/AU2016/000105 on Mar. 24, 2016, now abandoned.

(51) Int. Cl.
| | |
|---|---|
| *A61K 31/198* | (2006.01) |
| *A61K 9/00* | (2006.01) |
| *A61K 9/14* | (2006.01) |
| *A61K 31/375* | (2006.01) |
| *A61K 31/4415* | (2006.01) |
| *A61K 31/51* | (2006.01) |
| *A61K 31/7004* | (2006.01) |
| *A61P 25/32* | (2006.01) |

(52) U.S. Cl.
CPC .......... *A61K 31/198* (2013.01); *A61K 9/0095* (2013.01); *A61K 9/145* (2013.01); *A61K 31/375* (2013.01); *A61K 31/4415* (2013.01); *A61K 31/51* (2013.01); *A61K 31/7004* (2013.01); *A61P 25/32* (2018.01); *A61K 9/009* (2013.01)

(58) Field of Classification Search
CPC ... A61P 25/32; A61K 31/375; A61K 31/4415; A61K 31/51
See application file for complete search history.

(56) References Cited

U.S. PATENT DOCUMENTS

| 8,440,241 B1 | 5/2013 | Grady |
| 8,440,242 B1 | 5/2013 | Grady |
| 2005/0271754 A1 | 12/2005 | Cochrane |

FOREIGN PATENT DOCUMENTS

| CN | 101766637 B | 8/2012 | |
| CN | 101766716 B | 8/2012 | |
| CN | 101766672 B | 10/2012 | |
| JP | 04-342528 A | 11/1992 | |
| JP | H04342528 A | * 11/1992 | ........... A61K 31/195 |
| WO | 2008/021861 A2 | 2/2008 | |
| WO | 2012/027603 A2 | 3/2012 | |

OTHER PUBLICATIONS

European Patent Office, Communication pursuant to Article 94(3) EPC, dated Apr. 12, 2021, pp. 1-8.
Chisato Nishikawa, Vanderbilt University, Health Psychology Home Page, "The Best Hangover Treatment: What Is It?", Oct. 6, 2009, pp. 1-13.
Mintel, Reset, "After Drink for Hangovers" May 2015, , retrieved from http://www.gnpd.co, pp. 1-3.

* cited by examiner

*Primary Examiner* — Pancham Bakshi
(74) *Attorney, Agent, or Firm* — Orbit IP, LLP (57) ABSTRACT

A formulation and a method for treating, preventing or ameliorating or alleviating in a patient the symptoms of hangover, or veisalgia, associated with a bout of excessive alcohol consumption are disclosed. More specifically, a formulation comprising L-cysteine, thiamine and pyridoxine and a method for treating, preventing, ameliorating, or alleviating in a patient one or more of the symptoms of nausea, headache, diminished concentration, malaise and/or tiredness, and a desire to consume greasy and/or fatty and/or oily foods, associated with a bout of excessive alcohol consumption are disclosed.

6 Claims, 8 Drawing Sheets

FORMULATION AND METHOD FOR THE PREVENTION AND/OR TREATMENT OF HANGOVER SYMPTOMS

FIELD OF THE INVENTION

The invention relates to formulations and methods for the prevention and/or treatment of hangover symptoms associated with alcohol consumption.

BACKGROUND TO THE INVENTION

Alcohol induced hangover, also known as veisalgia, is a syndrome comprised of a range of symptoms including nausea, headache, diminished concentration, malaise and/or tiredness, and a desire to consume greasy and/or fatty and/or oily foods (amongst others) that typically occurs the day following overindulgence in alcohol. Although the precise pathogenesis of hangover is not known and likely to be due to multiple factors, there is considerable evidence that the accumulation of acetaldehyde plays a significant role [14, 15, 16, 17]. Alcohol is rapidly metabolized to acetaldehyde by the enzyme alcohol dehydrogenase. Acetaldehyde is then metabolized by aldehyde reductase to acetate.

The following formulas illustrate these reactions:

$$CH_3CH_2OH + NAD^+ \rightarrow CH_3CHO + NADH + H^+ \quad 1)$$

$$\text{Acetaldehyde} + NAD^+ + \text{Coenzyme A} \leftrightarrow \text{Acetyl-CoA} + NADH + H^+ \quad 2)$$

Acetate is excreted from the body via urine. However, when too much alcohol is consumed the body is overwhelmed and cannot effectively metabolize all the acetaldehyde that is being produced.

Patients who are genetically deficient in aldehyde reductase, or who are taking drugs which inhibit aldehyde reductase, experience very unpleasant side effects similar to those that occur in hangover [1,16]. Alcohol induced hangover is responsible for a significant degree of morbidity in the community and it is responsible for a high level of loss of productivity due to absenteeism from work and poor work performance [10, 12, 15].

Alcohol consumption increases each year. Due to side effects such as headache, nausea and a general feeling of malaise many hours of work and relaxation time are lost because of the inability to be productive. In Australia, the loss of productivity to alcohol was reported in 2005 to equate to AUD$1.2 billion. By 2013, this amount had risen to AUD$6 billion [12].

There are some products readily available in the Australian market (and other markets) that are advertised as a cure for hangover. However, PubMed database searches of the ingredients variously contained in those products reveal that none of them have been studied, other than Red Ginseng and glucose [6, 19]. The ingredients searched are as follows. The first four are listed separately because comments are made on them here. The balance is listed consecutively in the same bullet point:

Alanine—this ingredient is present in Red Ginseng. It has been shown to lower alcohol levels and partly relieve hangover in healthy men [6]. No relevant data was identified for alanine as an individual component, outside of Red Ginseng.

Lyscine hydrochloride—this ingredient is present in Red Ginseng. It has been shown to lower alcohol levels and partly relieve hangover in healthy men [6]. No relevant data was identified for Lyscine as an individual component, outside of Red Ginseng.

Glucose—This ingredient has been studied, but was shown to have no effect on symptoms of hangover [19].

*Pueraria lobata*—See comment below.

Asparginine; d-I alphatocopheryl acetate; Ferrous fumarate; Glutamine; Glycine; Ascorbic acid; Histidine; Isoleucine; Magnesium aspartate; Cysteine; Methionine; Nicotinamide; Phenylalanine; Proline; R-S alphalipoic acid; Riboflavine; Thiamine hydrochloride; Serine; Threonine; Tyrosine; Valine; Pyridoxine; Choline; Lecithin; Cyanocobalamin and Calcium pantothenate.

Furthermore, at least two of the readily available products in the Australian market contain the active ingredient *Pueraria lobata* which has been shown to increase acetaldehyde toxicity rather than reduce it [9]. *Pueraria lobata* root (or Kudzu root) has been reported to antagonize aldehyde reductase (in a similar manner to the drug disulfiram) and to elevate serum acetaldehyde levels potentially producing a disulfiram like reaction.

Specifically, disulfiram is prescribed for alcohol dependent persons because if they consume alcohol while taking disulfiram they experience very unpleasant adverse reactions such as flushing, nausea and headache which are features also seen in hangover. In addition, there is evidence that elevations in plasma acetaldehyde may be carcinogenic [8, 9]. This is concerning.

The literature describes hangover as being due to a combination of factors including acetaldehyde accumulation, dehydration and the effects of congeners. Nonetheless, the inventors have found that there has been relatively few suitable studies done to properly determine the cause of, or treatment for, hangover symptoms for a wide variety of reasons, including because, for example, alcohol studies cannot meaningfully be carried out in a laboratory atmosphere (as that would not be indicative of the natural way alcohol is consumed), of ethical considerations, hangover is complicated, and of the possibility or probability of great variation in symptoms between individuals, to name a few.

Moreover, currently available formulations for the prevention and/or treatment of hangover have many shortcomings the most important being the assessment of efficacy in a properly conducted clinical trial. There is a need for a formulation that prevents, alleviates, ameliorates or treats the symptoms of hangover.

The inventors have identified a novel formulation and method of administration that, in a suitable trial environment, have now been shown to provide a considerably greater effect than would be expected, or that could be expected of the currently available products researched by them in Australia.

Any reference to or discussion of any document, act or item of knowledge in this specification is included solely for the purpose of providing a context for the present invention. It is not suggested or represented that any of these matters or any combination thereof, formed at the priority date, part of the common general knowledge, or was known to be relevant to attempt to solve any problem with which this specification is concerned.

SUMMARY OF THE INVENTION

In this specification, unless stated otherwise, the phrase "a bout of excessive alcohol consumption" is intended to mean an episode during which a person consumes a sufficient quantity of alcohol, such that his/her blood alcohol concentration reaches or exceeds 0.05 grams per 100 millilitres of blood, or, under all the circumstances, would reasonably be expected to reach or exceed or have reached or exceeded 0.05 grams per 100 millilitres of blood.

Depending on some of the circumstances, and on the kind of, quantity of and speed with which, alcohol is consumed, among other factors, the episode of some preferred embodiments would typically (though not always) span a period of approximately 30 minutes to approximately 360 minutes. In some, perhaps more common, cases (and embodiments) the episode will last for approximately 120 minutes, or more.

Another factor that is likely to have a bearing on the length of such an episode, in preferred embodiments, is the gender of the person consuming alcohol. For example, to reach or exceed a blood alcohol concentration within approximately 120 minutes, a woman may need to consume approximately 4 standard drinks, while a man may need to consume approximately 5 to approximately 6 standard drinks.

Whether or not the amount of alcohol consumed is "excessive" within the meaning of the phrase "a bout of excessive alcohol consumption" is also dependent, in preferred embodiments, on several circumstances, factors and variables, including those mentioned above. Typically (though not always), "excessive" alcohol consumption would be, for example, the consumption by a women of approximately 6 to approximately 8 standard drinks over a period of approximately 360 minutes to approximately 480 minutes, and by a man of approximately 8 to approximately 12 standard drinks over approximately the same period of time.

According to a first aspect, the present invention provides a formulation for treating, preventing, ameliorating or alleviating in a patient symptoms of hangover, or of veisalgia, associated with a bout of excessive alcohol consumption, the formulation comprising:
 a therapeutically effective amount of L-cysteine;
 a therapeutically effective amount of thiamine; and
 a therapeutically effective amount of pyridoxine.

In some preferred embodiments, the formulation further comprises a therapeutically effective amount of ascorbic acid, and in some of the same, and in some other, preferred embodiments, the formulation further comprises a therapeutically effective amount of glucose.

A variety of embodiments of the invention provide that L-cysteine is included in the formulation in the range of approximately 20% to 40% w/w, more preferably, approximately 25% to 35% w/w, and more preferably still in the range of approximately 28% to 32% w/w. In some particularly preferred embodiments, L-cysteine is included in the formulation in a relative quantity of approximately 30.77% w/w.

According to several embodiments, thiamine is included in the range of approximately 0.3% to 4.9% w/w, more preferably, approximately 1.0% to 4.2% w/w, and more preferably still in the range of approximately 1.8% to 4.1% w/w. The formulation of some particularly preferred embodiments provide that thiamine is included in a relative quantity of approximately 2.56% w/w.

In several embodiments, pyridoxine is included in the formulation in the range of approximately 3.0% to 7.26% w/w, more preferably, approximately 4.2% to 6.06% w/w, and more preferably still in the range of approximately 4.9% to 5.36% w/w. Particularly preferred embodiments provide that pyridoxine is included in the formulation in a relative quantity of approximately 5.13% w/w.

Several of the embodiments of the formulation that further comprise ascorbic acid provide that the ascorbic acid is included in the range of approximately 20% to 40% w/w, more preferably, approximately 25% to 35% w/w, and more preferably still in the range of approximately 28% to 32% w/w. Several embodiments of such formulations provide that the ascorbic is included in a relative quantity of approximately 30.77% w/w.

In several embodiments in which glucose forms part of the formulation, the glucose is included in the range of approximately 20% to 40% w/w, more preferably, approximately 25% to 35% w/w, and more preferably still in the range of approximately 28% to 32% w/w. Several embodiments of such formulations provide that the glucose is included in a relative quantity of approximately 30.77% w/w.

According to several preferred and alternative embodiments, the L-cysteine is provided crystalline form, and in several such embodiments, it is provided as an anhydrous hydrochloride salt.

The thiamine included in preferred and alternative embodiments is provided in crystalline form, preferably as a hydrochloride salt.

In several preferred and alternative embodiments, the pyridoxine is provided in crystalline form, preferably as a hydrochloride salt.

Several of the embodiments of the formulation that further comprise ascorbic acid provide that the ascorbic acid is provided in crystalline form.

Several of the embodiments of the formulation that further comprise glucose provide that the glucose in crystalline form, preferably as dextrose monohydrate.

According to a particularly preferred embodiment of the formulation, the % w/w for each of the active ingredients equates to the following approximate quantities:
 L-cysteine—600 mg
 Thiamine—50 mg
 Pyridoxine—100 mg
 Ascorbic acid—600 mg
 Glucose—600 mg Some preferred and alternative embodiments of the formulation further comprise one or more excipients, being excipients selected as suitable for the formulation manufactured for particular routes of administration.

Persons skilled in the art could readily select appropriate excipients for use with formulations for different routes of administration. In some of the particularly preferred embodiments, the formulation does not contain any excipients.

The formulation of some embodiments further comprises one or more flavouring agents. Preferably, the flavouring agents are selected from the group consisting of one or more of Trusil Natural Orange 171063, Trusil Natural Lime flavour 169422, Trusil Natural Lemon flavour 168162, and Trusil Pineapple Hawaii 173920. However, persons skilled in the art would readily appreciate that a wide variety of flavouring agents could be used. In some particularly preferred embodiments, the flavouring agent is Trusil Natural Orange 171063.

In some of the embodiments, the formulation does not contain any flavouring agents.

In some preferred embodiments of the formulation, each active ingredient is provided as a powder. In some such, and in other, embodiments, all actives, excipients, and any flavouring agents, are provided in powder form.

Preferably, the formulation is provided as a blended powder. However, the formulation can also be provided in other forms including one or more of those selected from the group consisting of dispersible granules, tablets, caplets, capsules containing the blended powder, forms suitable for rectal administration, in liquid forms prepared for oral or for intravenous administration, patches for transcutaneous administration, or forms suitable for nasal administration.

In some particularly preferred embodiments, one or more doses of the formulation is/are provided in one or more sachets.

According to a second aspect, the present invention provides a product for use in the treatment, prevention, amelioration or alleviation in a patient of symptoms of hangover, or of veisalgia, associated with a bout of excessive alcohol consumption, the product comprising at least one sachet containing the formulation of the first aspect of the invention.

In some embodiments, the product comprises at least two sachets, with each sachet containing one dose of the formulation of the first aspect. The invention envisages that the product of preferred and of alternative embodiments may include several such sachets.

In preferred some embodiments, at least two sachets are tearably joined together along at least one edge of each sachet. The tearable join can be created by any suitable means, including for example a plurality of adjacent perforations along a suitable tear line.

In some embodiments wherein the product comprises several such sachets, there can be a tearable join between each sachet along at least one edge of each sachet. In some such embodiments, the tear difficulty of the tearable joins can be varied.

For example, the tear difficulty can alternate such that it is, for example, relatively easier to separate two sachets at a time from a length of sachets (than it would be to separate each sachet from a pair). Such embodiments facilitate dispensing of the product in pairs of sachets. Some of these embodiments are provided in the form of a reel, wherein the desirable number of sachets to be acquired can be dispensed by tearing the tearable join when the reel has been unwound sufficiently to expose the desired number of sachets.

The join between sachet can also take any one of a number other forms that will enable the sachets to be separated from one another with relative ease.

According to a third aspect, the present invention provides a container adapted to store at least one of the products according to the second aspect. In particularly preferred embodiments, the container is in the form of a box that takes the shape of a substantially rectangular prism and is adapted to contain several pairs of sachets. In such embodiments, the desired quantity of pairs of product can be dispensed relatively easily.

In a suitable variation for the container, and one that is particularly preferred, the upper half of the box in the shape of a substantially trapezoidal prism is removed, removable or not formed. Such an embodiment permits a greater area of a pair of sachets to be seen at one end of the box than of the other end of the box. Such embodiment is a preferred form of 'point-of-sale' container for the product.

In a fourth aspect, the present invention provides a method of treating, preventing, ameliorating or alleviating in a patient symptoms of hangover, or of veisalgia, associated with a bout of excessive alcohol consumption, the method comprising:
 a. administering to the patient a first dose of the formulation of the first aspect; and
 b. administering to the patient a second dose of the formulation of any of the first aspect between approximately 4 and approximately 10 hours after administration of the first dose.

In a fifth aspect, the present invention provides a method of treating, preventing, ameliorating or alleviating in a patient symptoms of hangover, or of veisalgia, associated with a bout of excessive alcohol consumption, the method comprising:
 a. administering to the patient a first dose of the formulation contained in the product of the second aspect; and
 b. administering to the patient a second dose of the formulation of the second aspect between approximately 4 and approximately 10 hours after administration of the first dose.

The method of the fourth and fifth aspects wherein the first dose and the second dose contain active ingredients in the amount/s discussed above.

The first dose is preferably taken immediately, or within approximately 5 to approximately 60 minutes after the last alcoholic beverage consumed during the bout. In alternative embodiments, the first dose is taken within approximately 5 minutes to approximately 240 minutes after the last alcoholic beverage consumed during the bout, more preferably within approximately 60 minutes to 180 minutes after the last alcoholic beverage consumed during the bout.

Preferably, at the appropriate time, each dose is mixed in a glass of water, or in another beverage (preferably, other than one containing alcohol), and stirred into the drink.

Preferably, the symptoms of hangover, or of veisalgia, treated, prevented, ameliorated or alleviated in a patient include one or more of the following symptoms: nausea, headache, diminished concentration, malaise and/or tiredness, and a desire to consume greasy and/or fatty and/or oily foods. Other symptoms of hangover, or of veisalgia may additionally be treated, prevented, ameliorated or alleviated in a patient taking the formulation in therapeutic doses and/or in a therapeutic regime.

BRIEF DESCRIPTION OF THE DRAWINGS

Preferred embodiments of the invention will now be described and illustrated by reference to the accompanying drawings in which.

DETAILED DESCRIPTION OF PARTICULARLY PREFERRED EMBODIMENTS OF THE INVENTION

According to particularly preferred embodiments, the inventors have developed a novel formulation which, for the purpose of trials undertaken described in the Example given below, has been named CJ1484.

CJ1484 is a formulation comprised of vitamins and amino acids. The ingredients are non-toxic dietary compounds that are essentially free from side effects. In one of the preferred embodiments of the invention, which was used in this study, the formulation is in a powder form. All active ingredients are readily absorbed through the gastrointestinal tract.

CJ1484 comprises the following active ingredients:

(1) L-Cysteine

L-cysteine is an amino acid, one of the building blocks for proteins in humans. It was discovered in 1810 and found to be essential to the diet of humans. L-cysteine is produced in the body by the conversion from serine and methionine. It plays a crucial role in reversing oxidization in the liver partially due to conversion to glutathione. L-cysteine has been shown to enhance the breakdown and reduce the accumulation of acetaldehyde [4]. In addition, administration of L-cysteine to rats has been demonstrated to markedly reduce the mortality due to acetaldehyde poisoning [13, 14].

(2) Thiamine

Thiamine (vitamin B1) has been used in tablet form as a vitamin supplement over the last 70 years. Thiamine is on the World Health Organization's list of essential medicines. Thiamine was first documented in 1937 to be used for the treatment of beriberi (thiamine deficiency inducing heart failure). Thiamine is a water-soluble vitamin essential in all living organisms. There is currently no recommended dose however in western countries doses as low as 1 mg up to 500 mg have been used as a single dose [5].

There is some evidence that thiamine may enhance the effects of L-cysteine on diminishing acetaldehyde-induced toxicity [13]. The addition of thiamine to L-cysteine enhanced the ability of L-cysteine to reduce mortality in rats poisoned with acetaldehyde [13, 14].

To the inventors' knowledge, there has never been a trial in humans of the impact of adding Pyridoxine or Thiamine to L-cysteine with a view to having a positive impact on hangover symptoms.

(3) Pyridoxine

Pyridoxine may have anti-nausea and anti-emetic activity. There is also some documented evidence that an analogue of pyridoxine may attenuate the toxicity of acetaldehyde [7].

(4) Ascorbic Acid

Ascorbic acid was discovered in 1747. James Lind conducted the first clinical trial on 12 sailors using oranges and lemons for the treatment of scurvy. The treatment was successful. Since this time Vitamin C has been used as a common supplement to human diets. Unlike animals, humans cannot synthesize their own Vitamin C. Vitamin C is a highly effective antioxidant that contributes to the breakdown of acetaldehyde [2].

(5) Glucose

There is some evidence that heavy alcohol consumption may lower blood glucose levels, but some commentators have been referenced as saying that consumption of alcohol has no effect on glucose levels. Glucose has been demonstrated in humans to correct some of the metabolic changes that accompany hangover, but to have no effects on hangover symptoms [19].

The combination of the above listed five ingredients in a single dose or treatment regime has never been studied.

The table below this paragraph shows the recommended minimum and maximum doses of each of the above mentioned ingredients for specific conditions.

| Compound | Recommended Minimum Daily Intake | Recommended Maximum Daily Intake | Effective dose in rats* † | Preferred single dose in humans (4 g) |
|---|---|---|---|---|
| L-cysteine (anhydrous) | 150 mg | 1500 mg [7] | 34 mg | 1240 mg |
| Thiamine•HCl | 10 mg | Undefined [5] | 42 mg | 120 mg |
| Ascorbic acid | 65 mg | 2000 mg [4] | 50 mg | 1200 mg |
| Pyridoxine•HCl | 1 mg | 1000 mg [9] | n/a | 240 mg |
| Glucose (Dextrose) | n/a | n/a | n/a | 1180 mg |

It is important to note that L-cysteine has only been used for paracetamol overdose, so the above minimum and maximum doses are extreme and would not in the inventors' opinion be used for any other condition, based on clinical practices adopted as at the filing date of this application. Thiamine HCL has been used in the treatment of alcoholism. However, the maximum dose would be dependent on blood Thiamine levels. Ascorbic Acid is purely used as a vitamin supplement. Pyridoxine HCL is sometimes used for the treatment of nausea.

In the particularly preferred embodiment adopted in CJ1484, the % w/w quantities adopted for the formulation are as follows:

L-cysteine—30.77% w/w
Thiamine—2.56% w/w
Pyridoxine—5.13% w/w
Ascorbic Acid—30.77% w/w
Glucose—30.77% w/w In the formulation used in the trials described in the Example below, the % w/w for each of the active ingredients equated to the following approximate quantities:

L-cysteine—600 mg
Thiamine—50 mg
Pyridoxine—100 mg
Ascorbic acid—600 mg
Glucose—600 mg In order to evaluate the effects of CJ1484 relative to the symptoms of hangover or of veisalgia, the inventors developed and ran a double blind randomized placebo controlled crossover trial.

Example: A Double Blind Randomized Placebo Controlled Crossover Study to Assess the Effects of Compound CJ1484 on Alcohol-Induced Hangover For the purpose of the trial, CJ1484 was administered orally. The dosage regimen adopted for the study is a preferred regimen that enables the active ingredients to be maintained at therapeutically effective levels while alcohol and acetaldehyde remain in the body during and following a bout of excess alcohol consumption [1].

Pre-clinical studies include the prevention of liver damage and death due to acetaldehyde intoxication in rats by active ingredients selected for the formulation [13, 14]. No studies of the formulation or its components have previously been performed in man.

Anecdotal experience of administering CJ1484 to subjects consuming a considerable amount of alcohol show that it is effective in treating, preventing, alleviating or ameliorating hangover symptoms.

Methods

A two period, randomized, placebo controlled, double blind crossover design was used with a minimum of 6 days separating each study day.

The trial was conducted under the guidelines for Good Clinical Practice (GCP) which have their origin in the World Medical Association's Declaration of Helsinki. The Declaration of Helsinki was responsive to the regulations of the Nuremburg trials conducted after World War II. Its drafters sought to ensure that human subjects involved in clinical research would, in future, have their rights, safety and well-being placed above all other considerations in clinical research. The document has been revised several times since it was published in 1964.
(Australian Government Natural Health & Research Council Department of Industry & Science.)

Each subject gave written informed consent prior to any study procedure.

Population

Twenty subjects were enrolled in the study. The population consisted of male and female subjects aged 24 to 75 years, all of whom volunteered to participate. Female patients of child bearing potential had a pregnancy test prior to each visit. Female subjects who were pregnant were not permitted to participate.

Inclusion and Exclusion Criteria

In keeping with recommendations for studies of hangover, minimal exclusion criteria were applied [17]. Persons regularly consuming more than 100 grams of alcohol per day or who have a history of treatment for alcohol or other drug dependence were excluded. Persons who had experienced the symptoms of hangover and who knew how much alcohol intake was required to produce hangover symptoms were included. It was reinforced to the subjects that they must be willing to experience a hangover on at least one occasion during the study.

Study Compound

The components (and their respective % w/w quantities) in each dose of the preferred embodiment of the formulation used in the study, named CJ1484, are:
L-cysteine 30.77% w/w (an amino acid);
Pyridoxine 5.12% w/w (Vitamin B6);
Ascorbic acid 30.77% w/w (Vitamin C);
Thiamine 2.56% w/w (Vitamin B1); and
Glucose 30.77% w/w.

The placebo was an equivalent mass of glucose alone.

Study Design

The study was conducted in a home environment overnight, as it has been recommended by experts in the field that studies of hangover be performed in a natural setting and not in a research laboratory [17].

A party atmosphere was created on each occasion for the under 40-year-old subjects who attended the site. They were provided with finger food, followed by a barbeque consisting of steak, sausages, potatoes, two different salads and bread rolls. Dessert was Pavlova cake and fruit salad. Throughout the evening chips and nuts were also available.

The following group, aged 40 to 50 were provided with cheese and biscuits on arrival, and a sit down barbeque meal consisting of marinated chicken, kebabs, jacket potatoes, three different salads and Turkish bread. Dessert was Pavlova cake and fruit salad. Throughout the evening chips and nuts were also available.

The group of over 50 year olds had a formal dinner setting. Entrée was pumpkin soup. The main meal consisted of baked lamb and ham, roasted vegetables and garlic bread. Dessert was Pavlova cake and fruit salad, followed by after dinner mints and coffee.

The principal investigators and research staff were briefed and tasked to ensure full compliance by all participants with the study protocol. All subjects were monitored throughout the evening.

Each subject was administered alcohol in the drink of their choosing over a four (4) hour period in a standard measured glass. Subjects could consume alcohol at the rate and quantity of their choosing to achieve an intake that they expected would lead to hangover symptoms. Each glass was counted and it was planned to attempt to achieve a mean alcohol intake for each subject of approximately 100 grams during the four (4) hour alcohol intake period. No subject was permitted to drink more than 200 grams of alcohol on a given study night.

At the end of the alcohol intake period, the research staff mixed a first dose of the study compound and the placebo (2 grams of glucose was used for the placebo) into respective soft drinks adopting a code to ensure that neither they nor the subjects knew whether the subjects were taking the study compound or the placebo. The research staff provided each subject a blinded dose. A second blinded dose (prepared in the same way as the first blinded dose) of each of the study compound and placebo were mixed and given to each subject to consume any time between no less than 4 and no more than 10 hours after the first blinded dose (for example, if they wake during the night). A detailed discussion of the method used for blinding and randomization is provided below.

Subjects remained at the site overnight. After awakening the following morning, they were provided with breakfast consisting of cereal, yoghurt, fresh fruit, eggs, bacon and toast. Subjects made their own choices.

Prior to breakfast, subjects were asked to complete a series of visual analogue scales. The visual analogue scales assessed nausea, headache, quality of sleep, difficulty with cognition and the desire for fatty foods. Alcohol levels were monitored the morning after the alcohol consumption using a Lion Alco meter and no subject was permitted to leave unless his/her alcohol level was measured to be 0.000%.

The subjects were contacted by telephone after their second study day and asked to rate how they compared their two study days using a score between 0 and 10 after each of the study alcohol intake periods: 0 was feeling extremely poorly and 10 was extremely good. This sense of well-being was the primary endpoint of the study.

Four to six subjects were studied on each study evening and there were four research staff in attendance.

A resuscitation kit, Epi Pen and all appropriate safety equipment was on site in case of emergency.

The study was conducted over the period of 5 months.

Randomization Technique

Randomization was performed in blocks of four by an independent person not connected to the trial.

Active and placebo were measured into clear plastic resealed bags containing the appropriate number of grams of product or matching placebo. Two of these bags (active or placebo) were placed in an envelope and numbered. Each subject was provided with one envelope on each night of the trial. All product was kept in a locked cupboard. The preparation of the resealed bags and their placement in numbered envelopes was performed by the independent person who organised the randomization code and who held the randomization code until the study was completed.

Primary and Secondary End Points

The primary end point was to show that the compound improved general well being assessed by recollection of the two study periods, after each period had been completed. Secondary endpoints were the results of the visual analogue scales filled in the day after each study evening. Differences between study days for the visual analogue scales were analyzed using Student's Paired T Test for paired data. The primary end point was also analyzed using Student's Paired T Test for paired data. The reason for using Student's Paired T test for paired data in this study was because the number of points in each data set were at the same time and were organized in pairs in which there is a definite relationship between each pair of data points.

In our study, measurements were taken from the same subject, after administration of study drug on two occasions. For example, we used the Student's Paired T Test to determine the significance of a difference in well-being from the first data point to the second data point. Data are presented in the figures as the mean±the standard error of the mean.

Power Calculation

We did not know what the between day variability of the hangover severity experienced with alcohol intake would be, but expected that it would be less than 30%. We believed that any reduction in the primary end point of greater than 20% would be clinically important.

To calculate the number of subjects required to give the trial enough power to reach end points that are statistically significant, we assumed certain criteria. As we were not aware of any studies having been done in this area, we tended to assume what we believed would be the worst case scenario. For each subject we assumed a daily variability of the primary and secondary end points as 30%. This figure is relatively high. The sample size of 20 subjects gave us the ability to detect changes in both primary and secondary end points of a minimum of 20% improvement. Although this appears to be a small difference, we believe it is clinically significant. Indeed, a p value of <0.05 between the active and placebo therapies would be statistically significant using Student's Paired T test.

Primary End Point

The reported degree of well-being is reported by the subjects on the two study days by visual analog scale illustrated below.

Each subject is questioned as to a score out of 0-10 how they felt the day after their treatments. This was transferred to the visual analog scales for analysis. At this point in time neither staff nor subjects knew which day they were treated with CJ1484 (the active treatment) or the placebo (glucose powder that looks the same as the active treatment).

That information was only to be made available when all 20 subjects completed the trial and the code (un-blinded) was opened.

Visual Analog Scale

Figure 7:
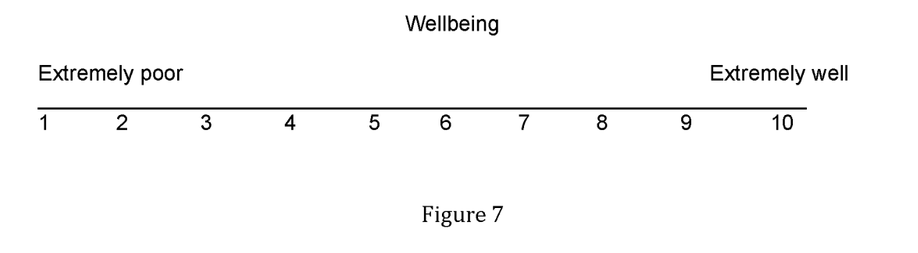
FIG. 7 is an example of one embodiment of the visual analog scale for a primary endpoint of wellbeing.

An example of one embodiment of the visual analog scale for a primary endpoint of wellbeing is illustrated in FIG. 7. This is the standardized 100 millimeter scale typically used in visual analog scales. When measuring the primary end point, subjects were asked to score wellbeing as a number between 0 to 10 as follows:

0—feeling extremely poorly
10—feeling extremely well

Results

Twenty subjects were randomized into the trial. One subject withdrew after the first study period because she became pregnant. This left 19 pairs of evaluable data.

The mean age of the patients was 47.7 years±14.3 years (range 21 to 72 years).

The mean alcohol intake during the active phase of the study was 108 grams±31 grams.

The mean alcohol intake during the placebo phase of the study was 104 grams±35 grams Primary Endpoint

TABLE 1

| Reported Wellbeing | Active | Placebo | P value |
| --- | --- | --- | --- |
| Scale of 0-10 Centimeters | 8.00 ± 0.92 | 3.47 ± 1.09 | P < 0.00001 |

This table shows that the average active score was 8.0 out of 10 with an above or below error of 0.92. The placebo score showed 3.47 out of 10 with an above or below error of 1.09. This table demonstrates that when taking CJ1484 the subjects' well-being was statistically greater than when only taking placebo.

The improvement in the primary endpoint on active compared to placebo was 177%.

P=<0.00001. Any P value less than P=<0.05 is significant. Accordingly, these results show major symptom relief with CJ1484. The smaller the p value the greater the certainty of the statistical significance. The statistical significance of this difference is high.

Secondary Endpoints—Visual Analogue Scales.

Figure 8:
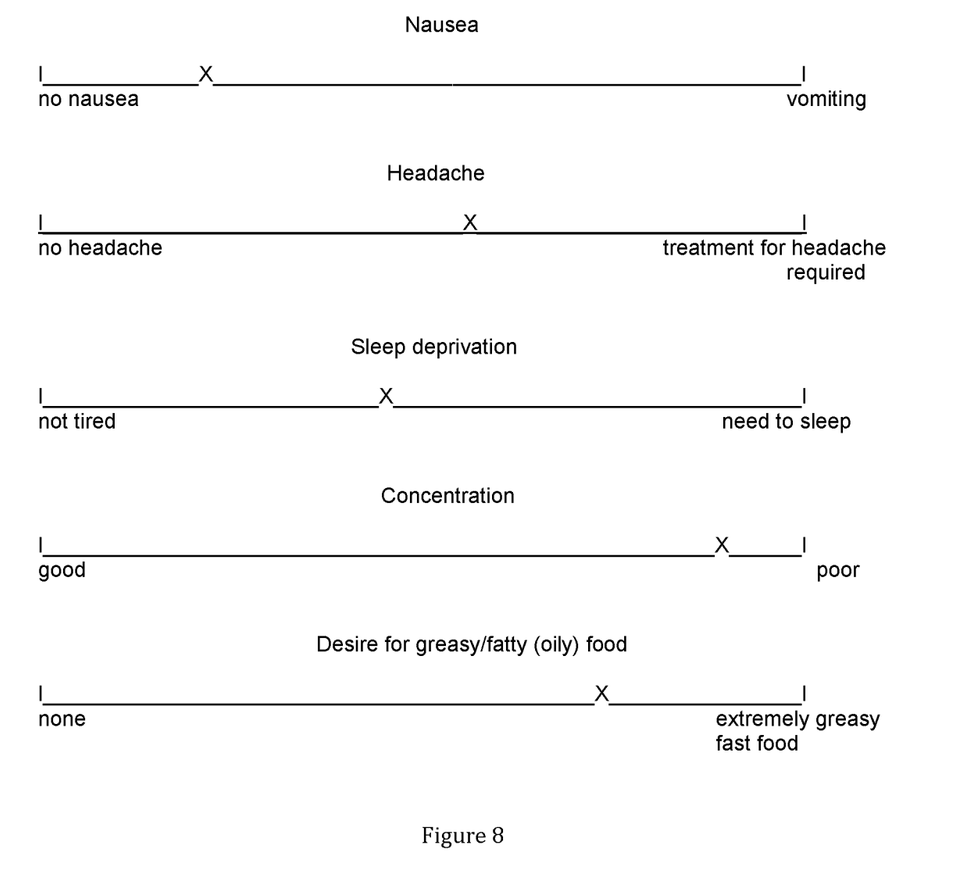
FIG. 8 is an example of one embodiment of the visual analog scales for secondary endpoints respectively: nausea, headache, sleep deprivation, concentration, and desire for greasy/fatty (oily) food, completed by a subject the morning after treatment the night before.

The visual analog scales were given to each subject the morning after their treatment night. They were asked to complete these before breakfast. If they felt poorly they made their mark toward the left. If they felt well they made their mark toward the right. An example of one embodiment of the visual analog scales for secondary endpoints respectively: nausea, headache, sleep deprivation, concentration, and desire for greasy/fatty (oily) food, completed by a subject the morning after treatment the night before is illustrated in FIG. 8.

Subjects were asked to place a cross (X) on the lines to best represent how they were feeling the following morning. This line is 100 millimeters, 0 being no side effects, 100 being illness. The location of each cross is then measured. In the above example, nausea would receive a score of 22, this is then calculated for both treatment days for each subject and then all subject data is pooled to arrive at a mean (or average) for all subjects with an above and below error (±) scored in millimeters.

The results in table 2 illustrate the reported outcomes by the subjects. The first column shows the five secondary outcomes the study considered. The second and third columns give the scores in millimeters for the two treatments. The last column shows the p value (measure of statistical significance) for each symptom.

TABLE 2

| Symptom | Active (0-100 mm) | Placebo (0-100 mm) | P value |
| --- | --- | --- | --- |
| Nausea | 36 ± 5 | 10 ± 3 | 0.0035 |
| Headache | 58 ± 5 | 18 ± 4 | 0.0003 |
| Poor sleep | 50 ± 5 | 35 ± 4 | 0.0291 |

TABLE 2-continued

| Symptom | Active (0-100 mm) | Placebo (0-100 mm) | P value |
|---|---|---|---|
| Poor concentration | 50 ± 5 | 21 ± 4 | <0.0001 |
| Desire for greasy/fatty (oily) food | 34 ± 6 | 22 ± 4 | 0.1453 |

This table as in table 1 shows the variation of the results between the different volunteers expressed as the SEM (standard error of the mean). The SEM becomes smaller as the number of people studied increases. It is an estimate of the true difference of the result between active and placebo if the entire population was studied.

Ethical Issues

Subjects were fully informed as to the risks and benefits of the trial. Potential risks associated with this study were the experience of hangover. There were no anticipated risks of the administration of the study compound.

DISCUSSION

The results of this study demonstrate that CJ1484 administered in the manner studied is capable of preventing, alleviating, ameliorating and/or treating the symptoms of hangover to a clinically significant extent. The principal finding is that the magnitude of the results of CJ 1484 on hangover symptoms far exceeded the results expected.

There have been articles suggesting that a study design like the one we have presented have been a long time overdue (17). As far as we can tell, no other researches have attempted this work. Alcohol studies such as this are difficult because they cannot be carried out in a laboratory atmosphere as that would not be indicative of the natural way alcohol is consumed.

This study has gone to extreme lengths to create the three most common venues for alcohol consumption—Party, Barbeque and Dinner party. We have also tried to capture an age range that is representative of drinkers. We excluded 18-24 year olds due to the possibility of non-compliance and drinking excessively without the investigators' knowledge.

Because hangover is complicated and has not been studied until now the primary endpoint of well-being was chosen. This is because of great variation in symptoms between individuals. Well-being was described to subjects as how they felt overall the following morning after a night of excessive drinking. Changes in the individual symptoms of hangover reflected the changes found for the primary endpoint of wellbeing.

The study supports our theory that 1-cysteine, by activating glutathione and accelerating acetaldehyde breakdown, aids in the prevention of acetaldehyde accumulation over the resultant genesis of hangover symptoms.

This finding is particularly surprising as hangover has been described as being due to a combination of factors including acetaldehyde accumulation, dehydration and the effects of congeners.

The secondary end points were essentially chosen as a breakdown of the primary endpoint. The major complaints from subjects who suffer from hangover were chosen eg: nausea, headache, sleep deprivation, concentration and the desire for greasy/fatty (oily) foods the following day.

The study has also shown that with the preferred dosing, together with compliance can achieve improvement over both primary and secondary endpoints.

The study did not attempt to include each of the active ingredients in CJ1484 because prior to this study a few of them have been shown to be less effective individually.

Although not all of the selected active ingredients in CJ1484 have been combined in a single formulation, each of them has been used in formulations either alone or in combination with less than the balance of them. Although the dosages at which each active ingredient has been used in such other formulations is not typically identical to the corresponding dosage used in CJ1484, the data from the study also supports the researchers' hypothesis that therapeutically suitable combinations of:

(1) L-cysteine, thiamine and pyridoxine;
(2) L-cysteine, thiamine, pyridoxine and ascorbic acid; and
(3) L-cysteine, thiamine, pyridoxine, ascorbic acid, and glucose; work synergistically to ameliorate, alleviate, prevent or treat the symptoms of hangover.

Product

As mentioned earlier, the present invention of particularly preferred embodiments also provides a product for use in the treatment, prevention, amelioration or alleviation in a patient of symptoms of hangover, or of veisalgia, associated with a bout of excessive alcohol consumption, the product comprising at least one sachet containing the formulation according to the invention.

Figure 1:
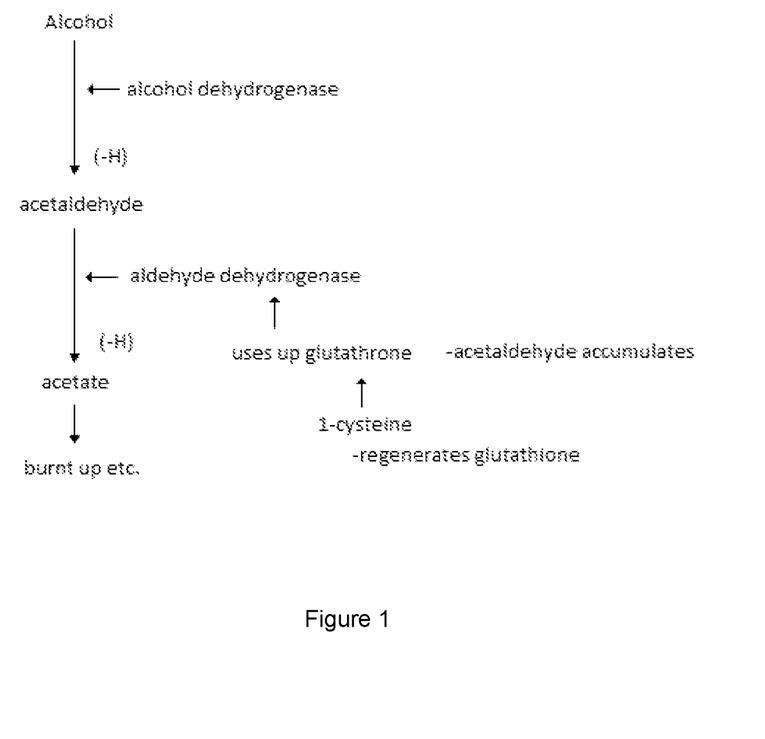
FIG. 1 is a schematic illustration of the metabolism of alcohol and the mode of action of l-cysteine.
Figure 2:
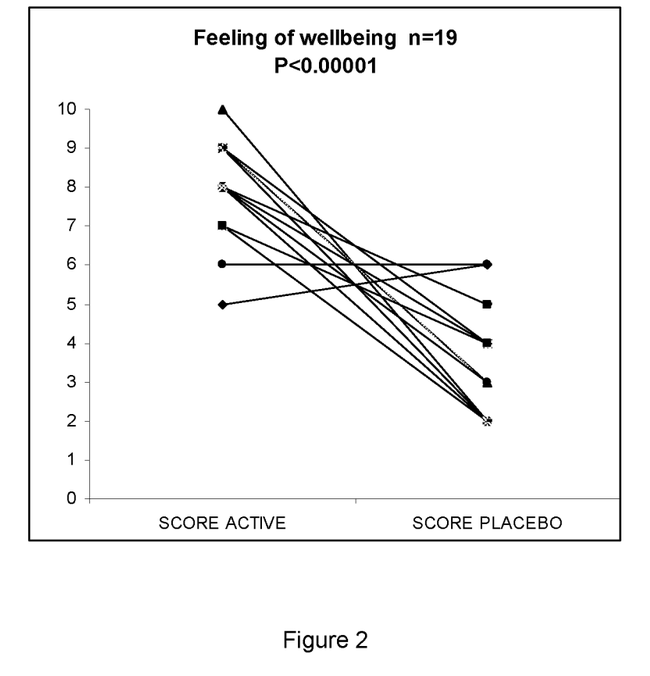
FIG. 2 is a graphical representation of changes in reported wellbeing between active and placebo study days for individual subjects.
Figure 3:
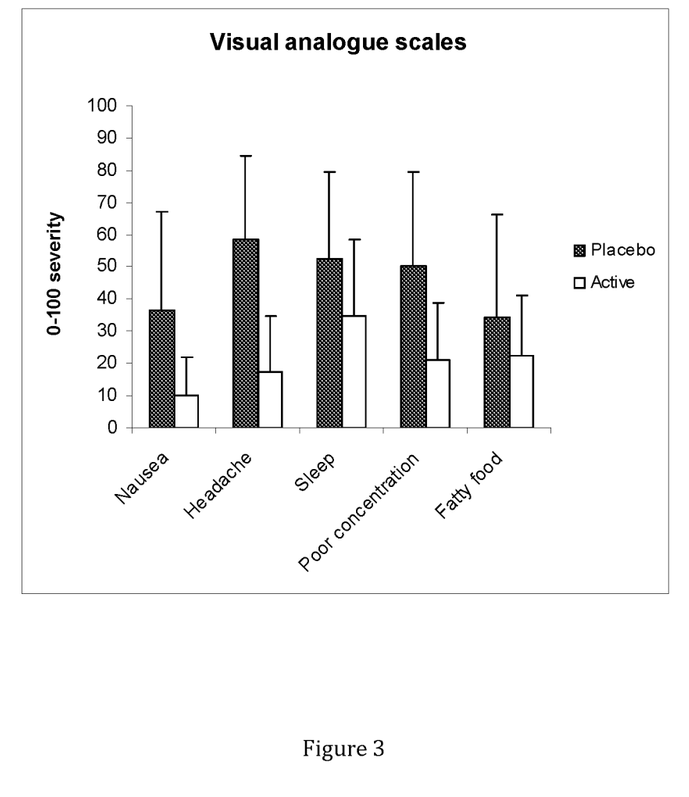
FIG. 3 is a graphical representation illustrating the results for visual analogue scales for active and placebo treatments. All differences were statistically significant except for the effects on desire for fatty foods (n=19).
Figure 4:
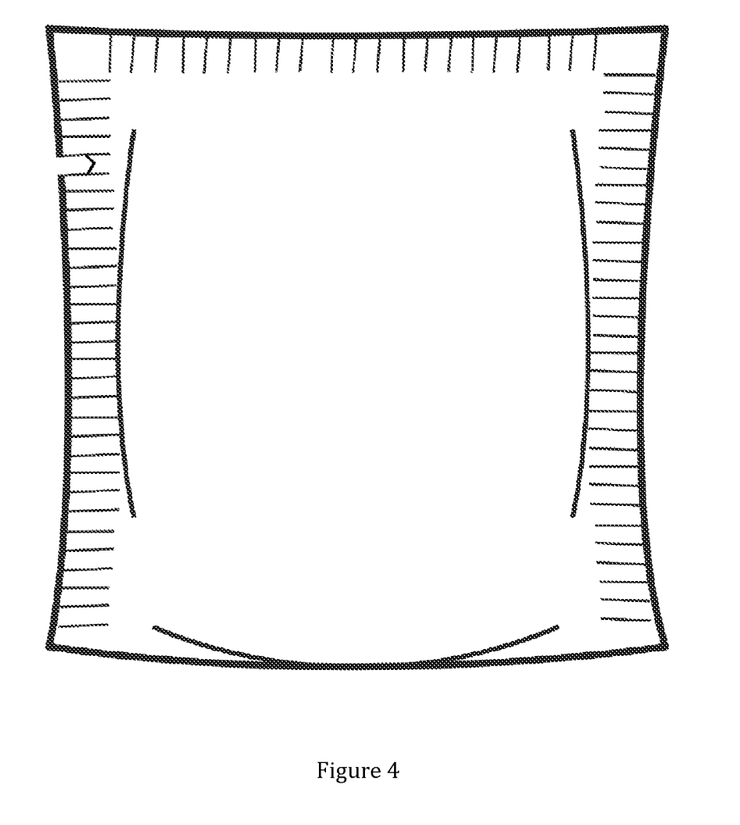
FIG. 4 is a schematic diagram of a sachet containing the active ingredients of a preferred embodiment of the invention.

FIG. 4 depicts a sachet made according to a preferred embodiment of the invention. A small notch (no numbered) to the upper-left corner of the sachet (as presented) is provided to facilitate a user opening the sachet to access its contents, or more specifically to enable a user to readily empty the content into, for example, a beverage.

Figure 5:
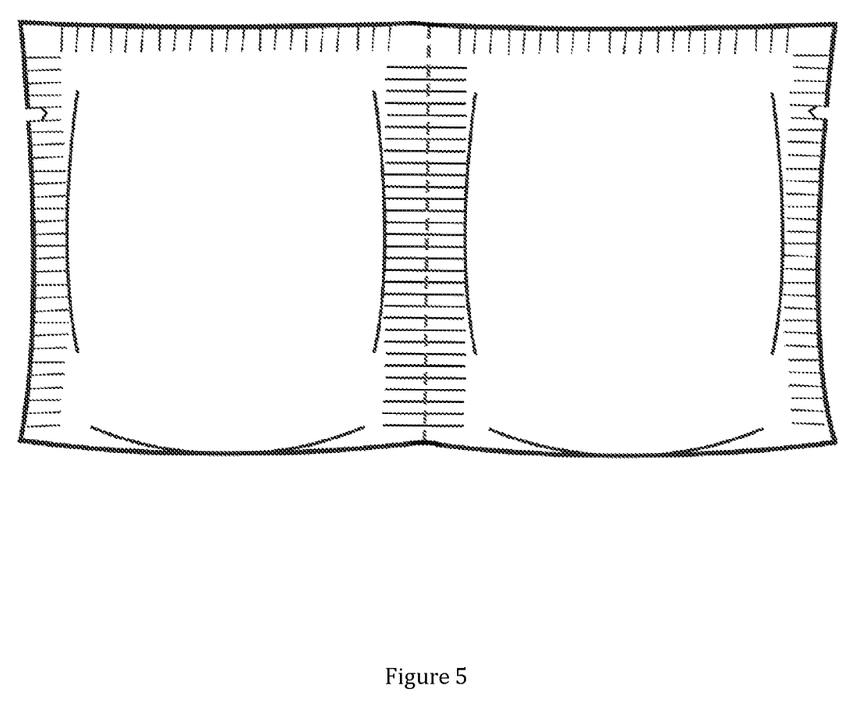
FIG. 5 is a schematic diagram showing two sachets tearably joined together, with each sachet containing the active ingredients of a preferred embodiment of the invention.

In some other particularly preferred embodiments, the product comprises at least two sachets, with each sachet containing one dose of the formulation. A representation of one such embodiment is depicted in FIG. 5. A dotted line drawn between the two sachets illustrates a preferred form of tearable join between them.

Container

Figure 6A:
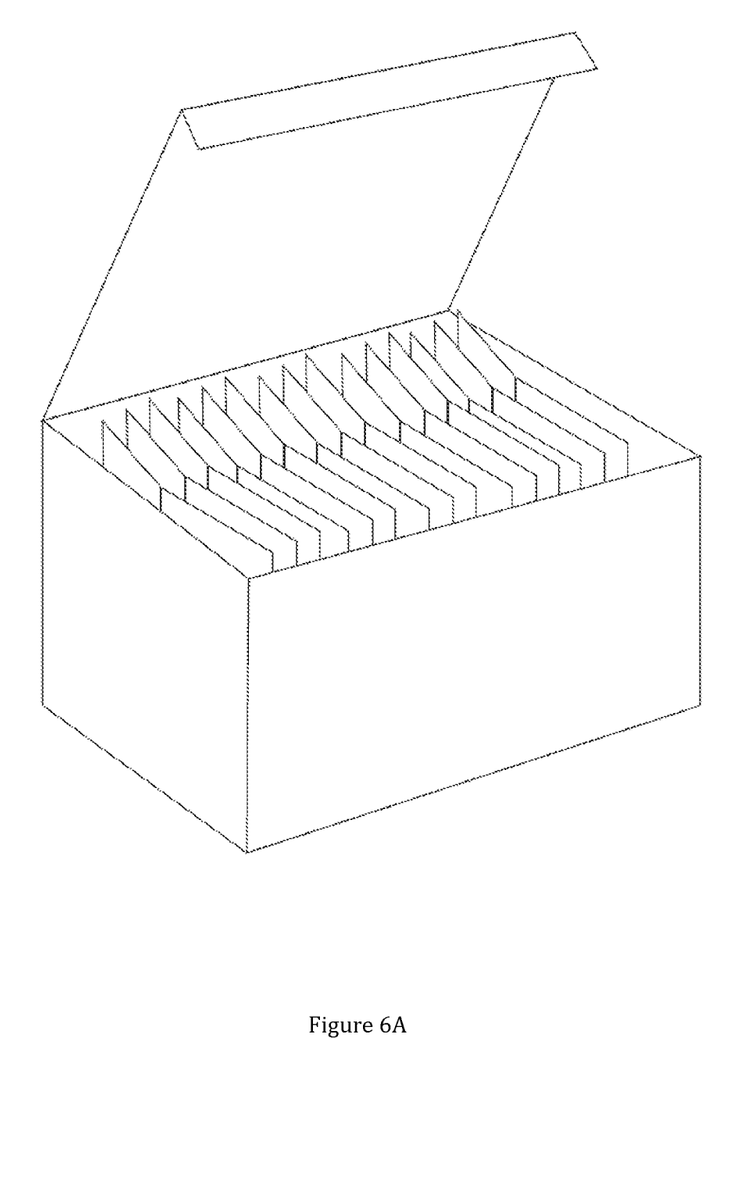
FIG. 6A is a schematic diagram showing a container containing several sets of sachets as depicted in FIG. 5.

The present invention also provides in particularly preferred embodiments a container adapted to store at least one of the product forms described above. In particularly preferred embodiments, the container is in the form of a box that takes the shape of a substantially rectangular prism and is adapted to contain several pairs of sachets. In such embodiments, the desired quantity of pairs of product can be dispensed relatively easily. This embodiment is depicted in FIG. 6A.

Figure 6B:
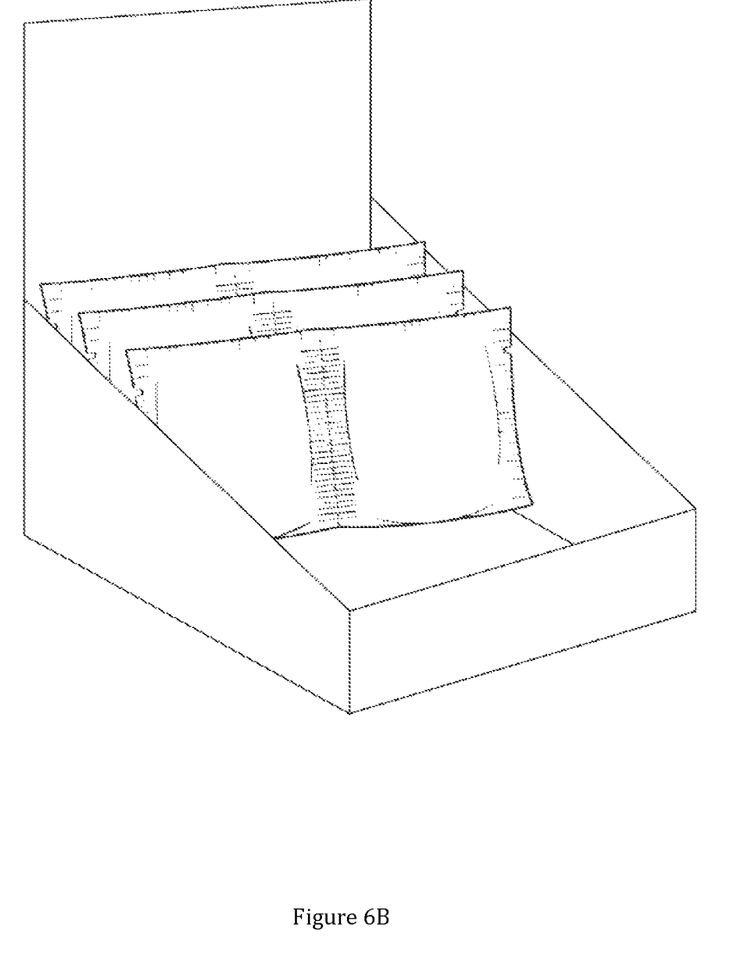
FIG. 6B is a schematic diagram showing a container (which is has a different shape and configuration to that depicted in FIG. 6B) containing several sets of sachets as depicted in FIG. 5.

In a suitable variation for the container, and one that is particularly preferred, the upper half of the box in the shape of a substantially trapezoidal prism is removed, removable or not formed. As depicted in FIG. 6B, such an embodiment permits a greater area of a pair of sachets to be seen at one end of the box than of the other end of the box. Such embodiment is a preferred form of 'point-of-sale' container for the product.

Method of Treatment/Prevention/Administration

According to a particularly preferred embodiment, the present invention provides a method of treating, preventing, ameliorating or alleviating in a patient symptoms of hangover, or of veisalgia, associated with a bout of excessive alcohol consumption, the method comprising:

a. administering to the patient a first dose of the formulation contained in a sachet as described above; and
b. administering to the patient a second dose of the formulation contained in a sachet as described above between approximately 4 and approximately 10 hours after administration of the first dose.

The first dose is preferably taken immediately, or within approximately 5 to approximately 60 minutes after the last alcoholic beverage consumed during the bout.

Preferably, at the appropriate time, each dose is mixed in a glass of water, or in another beverage (other than one containing alcohol), and stirred into the drink.

The second dose is likely to be taken during arousal of a sleep after the bout. Accordingly, it is recommended that the second dose be prepared and left near the bed, for example on the patient's bedside table so that when s/he reaches for a drink throughout the night, the drink consumed contains the second dose. However, the second dose may also be taken after the patient has awoken from a full night's sleep.

REFERENCES

[1] Debey, H. J., MacKenzie, J. B. & MacKenzie, C. C. (1958). The Replacement by Thiazolidinecarboxylic AcM of Exogenous Cystine and Cysteine, J. Nutr., 66, 607-619.
[2] Ginter, E., Zloch, Z., Ondreicka, R. (1998). Influence of vitamin C status on ethanol metabolism in guinea-pigs. Institute of Preventive and Clinical Medicine, Bratislava, Slovak Republic, 47(2), 137-41.
[3] Hald, J., Jacobsen, E. (1948). A drug sensitising the organism to ethyl alcohol Lancet, 2, 1001-1004.
[4] Institute of Medicine. Food and Nutrition Board. Dietary Reference Intakes for Vitamin C, Vitamin E, Selenium, and Carotenoids Washington, DC: National Academy Press, 2000.
[5] Institute of Medicine (US) Standing Committee on the Scientific Evaluation of Dietary Reference Intakes and its Panel on Folate, Other B Vitamins, and Choline. Washington (DC): National Academies Press (US); 1998.
[6] Lee, M. H., Kwak, J. H., Jeon, G., Seo, J. H., Lee, H. S., Lee, J. H. (2014) Red Ginseng relieves the effects of alcohol consumption and hangover symptoms in healthy men: a randomised crossover study. Food Funt 5(3): 528-34.
[7] Lheureux, P., Penaloza, A., Gris, M. (2005). Pyridoxine in clinical toxicology: a review. European Journal of Emergency Medicine, 12(2), 78-85.
[8] Lu, L., Liu, Y., Zhu, W., Shi, J., Liu, Y., Ling, W., Kosten, T. R. (2009) Traditional Medicine in the Treatment of Drug Addiction. The American Journal of Drug and Alcohol Abuse, Vol. 35, Iss. 1
[9] McGregor, N. R. (2007) *Pueraria lobata* (Kudzu root) hangover remedies and acetaldehyde-associated neoplasm risk. University of Melbourne, Faculty of Medicine, Dentistry and Health Sciences, Alcohol 41, 469-478.
[10] Olsen, R. E., (Eds M. G. Wohl and R. S. Goodhart; Lea and Febiger 1968). Nutrition and Alcoholism, in: Modern Nutrition in Health and Disease, p. 767-781.
[11] Perry, T. A., Weerasuriya, A., Mouton, P. R., Holloway, H. W., Greig, N. H. (2004). Pyridoxine-induced toxicity in rats: a stereological quantification of the sensory neuropathy. Exp Neurol, 190, 133-44.
[12] Roche, A., Pidd, K., & Kostadinov, V. (2015). Alcohol- and drug-related absenteeism: a costly problem. Australian and New Zealand Journal of Public Health.
[13] Sprince, H., Parker, C. M., Smith, G. G., & Gonzales, L. J. (1974). Protection against acetaldehyde toxicity in the rat by L-cysteine, thiamine, and L-2-methylthiazolidine-4-carboxylic acid. Inflammation Research, 4(2), 125-130.
[14] Sprince, H., Parker, C. M., Smith, G. G, & Gonzales L J. (1975). Protective action of ascorbic acid and sulfur compounds against acetaldehyde toxicity: implications in alcoholism and smoking. Agents Actions, 5(2), 164-73.
[15] Stephans, R., Verster, J. C. (2010) The importance of raising the profile of alcohol hangover research. Curr Drug Abuse Rev. June; 3(2):64-7.
[16] Verster, J. C. (2012) Editorial: The need for an effective hangover cure. Curr Drug Abuse Rev. March; 5(1):1-2.
[17] Verster, J. C., Stephens, R., Penning, R., Rohsenow, D., McGeary, J., Levy, D., McKinney, A., Finnigan, F., Piasecki, T. M., Adan, A., Batty, G. D., Fliervoet, L. A. L., Heffernan, T., Howland, J., Kim, D-J., Kruisselbrink, L. D., Ling, J., McGregor, N., Murphy, R. J. L., van Nuland, M., Oudelaar, M., Parkes, R., Prat, G., Reed, N., Slutske, W. S., Smith, G., Young, M., on behalf of the Alcohol Hangover Research Group. (2010) The alcohol hangover research group consensus statement on best practice in alcohol hangover research. Curr Drug Abuse Rev. 3(2): 116-126.
[18] Verster, J. C., Penning, R. (2010) Treatment and prevention of alcohol hangover. Curr Drug Abuse Rev. 3:103-109.
[19] Ylikahri, R. H., Leino, T., Huttunen, M. O., Poso, A. R., Eriksson, C. J., Nikkila. (1976) Effects of fructose and glucose on ethanol-induced metabolic changes and on the intensity of alcohol intoxication and hangover. Eur J Clin Invest. 6(1): 93-102.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

It is to be noted that, throughout the description and claims of this specification, the word "comprise" and variations of the word, such as "comprising" and "comprises", is not intended to exclude other variants or additional components, integers or steps. Modifications and improvements to the invention will be readily apparent to those skilled in the art. Such modifications and improvements are intended to be within the scope of this invention.

The invention claimed is:

1. A capsule formulation for treating, preventing, ameliorating or alleviating in a patient symptoms of hangover, or of veisalgia, associated with a bout of excessive alcohol consumption, the formulation comprising:
   600 mg of L-cysteine in crystalline form or as an anhydrous salt;
   50 mg of thiamine in crystalline form or as a hydrochloride salt;
   100 mg of pyridoxine in crystalline form;
   600 mg of ascorbic acid; and
   600 mg of glucose.

2. The formulation of claim 1, wherein the 600 mg of L-cysteine is 30.77% w/w of the formulation.

3. The formulation of claim 1, wherein the 50 mg of thiamine is 2.56% w/w of the formulation.

4. The formulation of claim 1, wherein the 100 mg of pyridoxine is 5.13% w/w of the formulation.

5. The formulation of claim 1, wherein the 600 mg of ascorbic acid is 30.77% w/w of the formulation.

6. The formulation of claim 1, wherein the 600 mg of glucose is 30.77% w/w of the formulation.

* * * * *